United States Patent [19]

Phillips

[11] Patent Number: 4,984,447
[45] Date of Patent: Jan. 15, 1991

[54] SOILS PERCOLATION TESTING APPARATUS

[76] Inventor: James L. Phillips, 3 Rosewood Dr., Little Rock, Ark. 72209

[21] Appl. No.: 401,835

[22] Filed: Sep. 1, 1989

[51] Int. Cl.⁵ .................... G01N 15/08; G01F 23/58
[52] U.S. Cl. ........................................ 73/38; 73/73
[58] Field of Search .................................. 73/38, 73

[56] References Cited

U.S. PATENT DOCUMENTS

| 3,892,126 | 7/1975 | Curtin | 73/38 |
| 3,945,247 | 3/1976 | Anderson | 73/73 |
| 4,099,406 | 7/1978 | Fulkerson | 73/73 |
| 4,182,157 | 1/1980 | Fink | 73/38 |
| 4,341,110 | 7/1982 | Block | 73/38 |
| 4,561,290 | 12/1985 | Jewell | 73/38 |

FOREIGN PATENT DOCUMENTS

| 658554 | 2/1963 | Canada | 73/38 |
| 2403545 | 5/1979 | France | 73/38 |
| 1203187 | 1/1986 | U.S.S.R. | 73/38 |
| 817295 | 7/1959 | United Kingdom | 73/38 |

Primary Examiner—Hezron E. Williams
Assistant Examiner—Joseph W. Roskos
Attorney, Agent, or Firm—Hermann Ivester

[57] ABSTRACT

A soils testing apparatus has a hollow shaft for insertion into a test hole and includes vertically adjustable wedging blades slidable and T-tracks on the shaft for centering alignment in the test hole. A hand pump evacuates water from the test hole to a predetermined null point whereupon vertical movement of a float and float rod supported and guided within the shaft over a finite period of time will yield a direct percolation absorption rate.

8 Claims, 2 Drawing Sheets

SOILS PERCOLATION TESTING APPARATUS

BACKGROUND OF THE INVENTION

1. Field of the Invention

This invention relates to soils percolation testing apparatus and more particularly relates to improvements in the art of determining the liquid absorptive rate of soil sites under investigation or examination.

2. The Prior Art

The prior art is characterized by large clumsy devices four inches or greater in diameter and requiring a power source, timers, recording media and they operate on the concept of recording the drop in water level over a finite period of time.

SUMMARY OF THE INVENTION

The primary objective of this invention is to provide an inexpensive, rugged, easily employed, highly accurate device for determining the liquid absorption rate of soils.

A small cylindrical shaft is secured in a test hole and is adjustably positioned with the use of vertically slidable blades so that it is virtually centered in an upright position. An integral hand operated pump is used to set the top of a float rod to a zero or null position, whereupon a time measurement is taken and after a predetermined time interval correlated with a calibrated scale, a direct reading of the absorption rate is obtained.

DESCRIPTION OF THE PREFERRED EMBODIMENTS

Although details of the present application can be varied dimensionally without departing from the principles of the present invention, a preferred embodiment will be described with the use of actual dimensions as utilized in an exemplification of the inventive subject matter.

Figure 1:
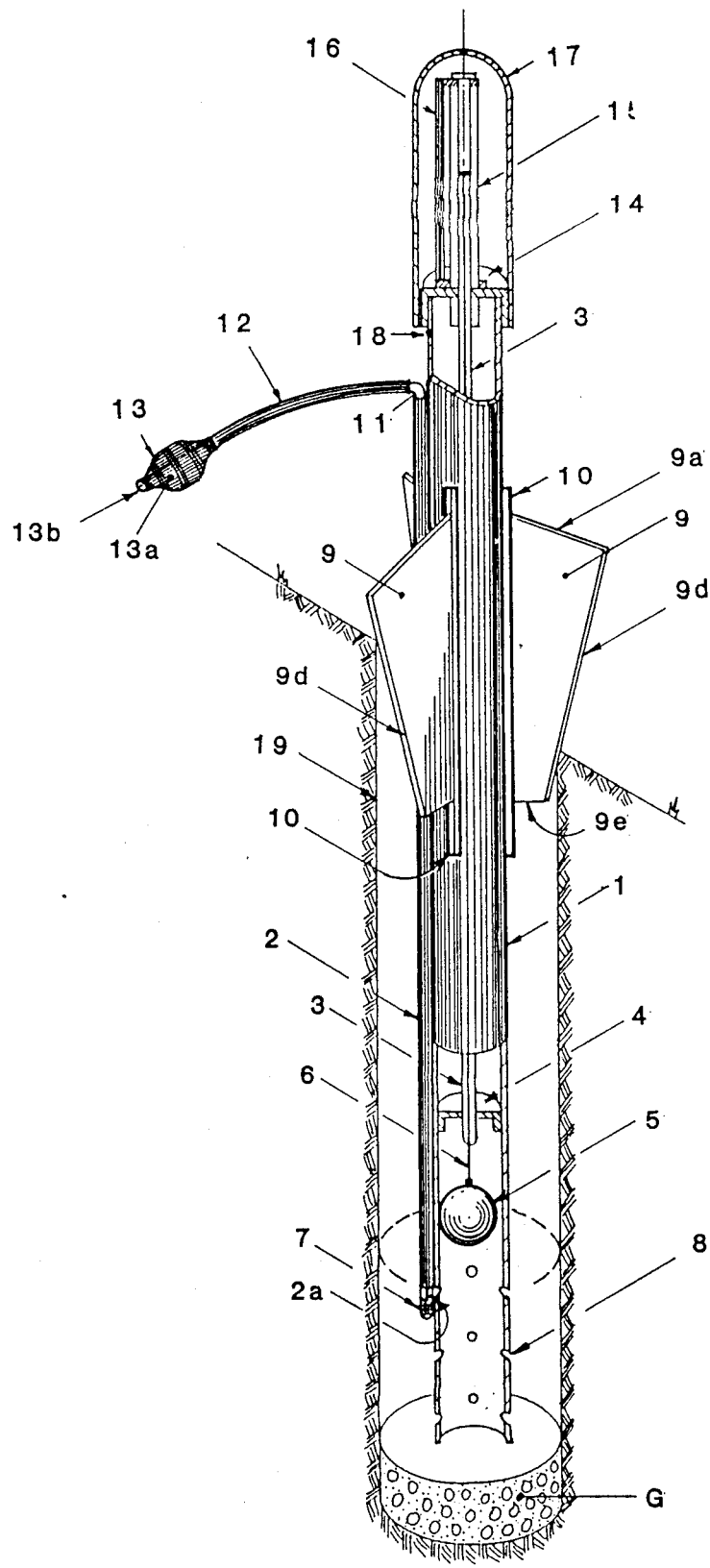
FIG. 1 is a perspective view of a testing apparatus positioned in a typical placement within a test hole.

Thus, referring to FIG. 1, a soils testing apparatus constructed in accordance with the present invention is shown disposed in a typical placement within a test hole. The apparatus comprises a 2 inch (5.08 cm.) diameter cylindrical shaft 1 which may be made of a suitable rigid plastic material.

The shaft 1 is approximately 36 inches (91.44 cm.) in length and forms a housing in which there is disposed a round buoyant float 5 which may also be made of a suitable plastic material, for example, the float 5 may be a hollow plastic molding. The float 5 is attached to a float rod 6, which may be formed as an extrusion from an acrylic plastic material. In the exemplification of the present embodiment, the float rod 6 is 0.125 inches in diameter (32 mm.) and 34.625 inches long (87.95 cm.). The upper 6 inches (15.24 cm.) is preferably a distinctive contrasting color, for example, a red color.

The float rod 6 is enclosed by a 0.375 inch (95 mm.) outside diameter clear extruded acrylic guide tube 3 which is particularly characterized at its upper end by a tube 15 which is approximately 6.5 inches (16.51 cm.) long and 0.625 inches (1.59 cm.) outside diameter marked with indicia means forming a graduated scale indicating the exact percolation rate calibrated in terms of time measured in minutes for 1 inch (2.54 cm.) of water to be absorbed by the adjacent soil.

Figure 6:
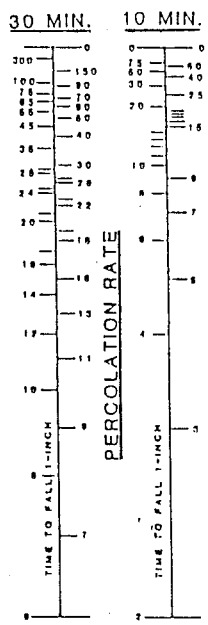

Referring to FIG. 6, the calibrated scales are illustrated. It will be noted that the scale on the left of FIG. 6 designates so-called 30 minute readings while the scale on the right hand side of FIG. 6 is calibrated for 10 minute readings.

In order to facilitate the ease of reading the percolation rate, a magnifying lens 16 is provided which is approximately 5 inches (12.7 cm.) long and is juxtaposed to the end of the float rod 6 and through which the end of the float rod 6 may be viewed relative to the graduated scales on the guide tube 15.

Figure 5:
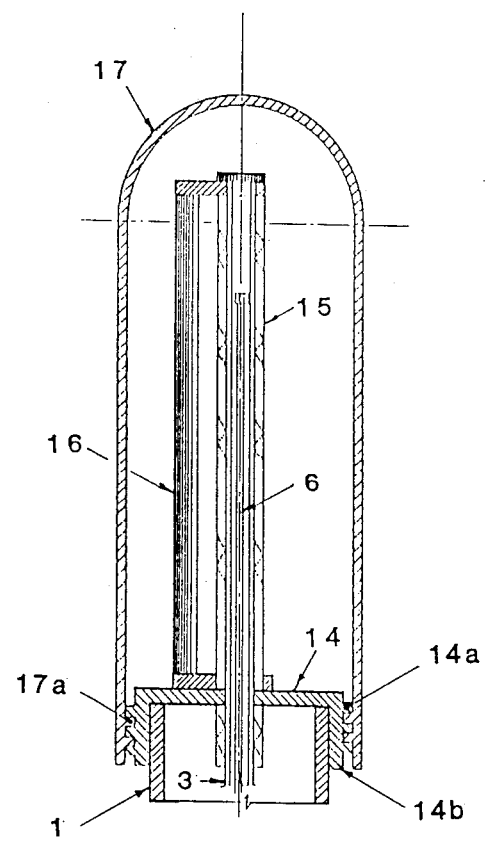
FIG. 5 is a cross-sectional view similar to the top portion of FIG. 1, but enlarged to show additional details of the invention; and, FIG. 6 is a front elevational view of the calibrated percolation rate scales used in the apparatus of the present invention.
Figure 2:
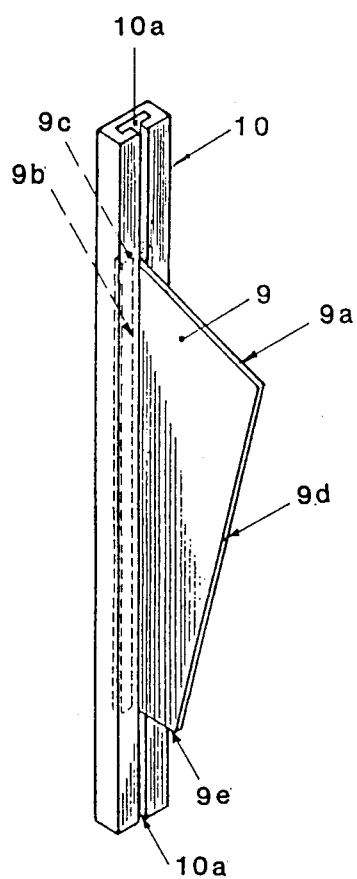
FIG. 2 is a fragmentary enlarged view showing additional details of the vertical alignment blades and the sliding track provided in accordance with this invention.

Referring to FIGS. 1 and 5, it will be noted that the entire upper assembly is enclosed and protected by a globe-like cap 17 made of an opaque plastic and having a cylindrical body portion which terminates in a rounded spherical dome at its uppermost end. The cylindrical body illustrated is approximately 3 inches in diameter (7.62 cm.) and is approxi-mately 9 inches (22.86 cm.) in longitudinal dimension. The bottom end of the cylindrical body portion of the cap 17 is formed with internal screw threads 17a for effecting screw threaded engagement with external screw threads 14 a formed on the external flange 14b provided on a cover member 14 which fits over the top end of the shaft 1.

Figure 3:
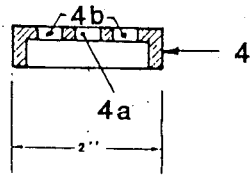
FIG. 3 is a bottom plan view of the lower end of the float rod guide tube spacer.
Figure 4:
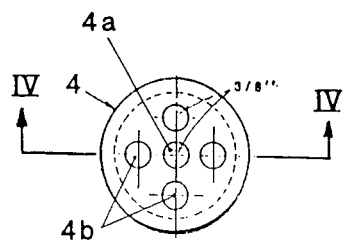
FIG. 4 is a cross-sectional view taken on line IV—IV of FIG. 3.

At the lower end of the float guide tube 3 there is provided a spacer 4 which is more particularly shown in FIGS. 3 and 4 in conjunction with FIG. 1. Thus, the spacer 4 made of plastic is essentially a flanged disc approximately 2 inches (5.08 cm.) in diameter and through which extends a centrally disposed opening 4a and four radially outwardly circumferentially spaced openings 4b, each being approximately 0.375 inches in diameter (95 mm.). The spacer 4 functions to hold the lower end of the tube 3 in proper position.

In accordance with this invention, the apparatus is also equipped with a hand operated suction pump shown generally at 13 and comprising a rubberized hollow bulb 13 a having the usual air check valve integrated in the end thereof as at 13b. The bulb 13a is connected to a flexible plastic tubing 12 which, in turn, is connected to a rigid suction tube 2 by way of an elbow 11. The tube 2 is disposed to extend generally downwardly on the outside of the shaft 1 and is of sufficient length to reach within 6 inches of the bottom of the shaft 1. Positioned at the lower end of the suction tube 2 is a foot valve 2 a with a strainer 7 which will maintain zero leakage.

In order to align the apparatus in a test hole accurately and quickly, the device of the present invention is particularly characterized by the utilization of three equiangularly spaced blades 9 carried and positioned in complementary shaped T-tracks 10 fastened in firm assembly with the outside surface of the shaft 1. Each blade 9 is a plate-form element having an upper edge 9a disposed at approximate right angles to a longitudinal edge 9b having a T-flange 9c formed thereon or attached thereto, and which has a sliding insert fitting relationship with an adjoining T-track member 10 having a T-shaped recessed track 10a formed therein to receive the corresponding flange 9c. The front edge of the blade 9 is a piloting edge 9d which tapers downwardly and inwardly and terminates in a bottom edge 9e disposed at right angles to the longitudinal edge 9b. Thus, as the device is placed into a test hole, the piloting edges of the blades 9 guide the apparatus into a properly centered upright position.

In order to properly ventilate the apparatus, an air vent hole 18 is formed by drilling and is located at the top of the shaft 1.

In operation, the percolation testing procedure is as follows:

First of all, a test hole 19 is dug in the site under investigation or examination approximately 4 to 12 inches (10.16 cm. to 30.48 cm.) in width and to the depth of the proposed absorption field, which is generally 24 inches (60.96 cm.) The bottom and the side walls of the test hole 19 are carefully scratched with a knife blade or a similar sharp pointed instrument in order to remove any smeared soil surfaces and to provide a natural soil interface into which water may percolate. All loose material is removed from the test hole. To protect the bottom of the hole from scouring and sediment, 2 inches (6.08 cm.) of coarse sand or fine gravel as shown at G is added.

The test hole 19 is then preconditioned or saturated by filling the hole 19 with clear water to a minimum of 12 inches (30.48 cm.) above the protective layer G and is maintained at such level overnight, or for at least a period of 4 hours. After completion of the saturation period, the water level is adjusted in the test hole to approximately seven inches above the gravel G. Thereupon, the apparatus including the shaft 1 is inserted into the test hole 19. The plastic blades 9 are inserted into the T track 10 and are vertically adjusted by engaging the wedging edges 9d against the sides of the test hole 19.

After securing the instrument properly in the test hole 19, the hand-held suction pump 13 is used to accurately set the top of the float rod 6 and the percolation rate scale 15 to 0 by carefully exhausting some remaining water in the test hole to approximately six inches above the gravel G. The time is recorded accurately and after a 30 minute period, the 30 minutes scale 15 is read. The reading is the desired absorption rate needed for design purposes.

In sandy soils or in such soils in which the first 6 inches of water seeps away in less than 30 minutes after the four hour saturation period, the time interval between measurement should be taken at approximately 10 minutes and a test run should be undertaken for one hour. The drop that occurs during the final 10 minutes is read on the 10 minutes scale 15 and is the desired absorption rate to be used for design purposes.

Although minor modifications might be suggested by those versed in the art it should be understood that I wish to embody within the scope of the patent warranted hereon all such modifications as reasonably and properly come within the scope of my contribution to the art.

I claim as my invention:

1. A soils testing apparatus, comprising, in combination, an elongated upright hollow cylindrical shaft having a lower end formed with side wall apertures over a predetermined discrete distance to allow water communication between the inside and outside of the shaft;

a plurality of circumferentially spaced longitudinal T-tracks fastened in firm assembly on the outside of said shaft;

a cap on the top of said shaft and a spacer in a lower intermediate portion of said shaft;

a float rod guide tube interiorly of said shaft and being supported by said spacer and said cap and extending upwardly outside of said shaft;

a float rod in said guide tube having a float depending from the bottom end thereof and having a free upper end extending outwardly of said shaft and having coloration means to enhance its visibility, said guide tube having graduated calibrated scale means at its upper end adjacent the free end of said float rod, and a plastic globe fastened to the top of said shaft to enclose and protect the top of the guide tube, the top of the float rod and the scale means;

pump means comprising a tubing element on the outside of said shaft and having a foot valve and strainer at the lower end thereof, said pump means including a hollow bulb means disposed in an accessible position exteriorly of said shaft; and blade means complementary to said T-track means and having tapered pivoting edges for wedging engagement with the sides of a test hole;

whereby said shaft can be inserted into a test hole and the blade means thereafter inserted into the T-track means and vertically adjusted to center the shaft in the test hole;

said pump being operable to evacuate water from the test hole to such a depth as to set the float to a zero or null position and to permit measured calibrated changes in the test hole as a function or percolation rates.

2. In a soils testing apparatus of the type including a vertical float, the improvement of a housing for the float having a plurality of circumferentially spaced T-track guides on the outside of said housing, and a corresponding plurality of guide blades each having a T-flange slidably insertable in one of said T-track guides and being vertical adjustable therein, each said blade having an external tapered edge for wedging engagement with an adjoining wall of a test hole;

whereby the housing may be inserted into a test hole and the blades may then be adjusted vertically until the housing is centered and wedged firmly in the test hole.

3. In a soils testing apparatus of the type including a hollow shaft insertable in a test hole and a vertical float means to measure calibrated changes in the test hole, the improvement of a hand pumping means comprising a hollow bulb exteriorly of the apparatus for activation by an operator and a tube for said apparatus to extend into a test hole and having a foot valve and a strainer at the end thereof for selectively evacuating water from the test hole to predeterminable limits.

4. In a soils testing apparatus as defined in claim 3, the improvement of a float means which comprises a float rod and a float guide tube for guiding said rod and having an upper clear end through which the movable end of said float rod may be viewed;

scale means on said upper end including calibrated graduated scales to measure the relative movement of the float rod; and a float on the bottom of said float rod to move said rod as a function of the water level in the test hole.

5. In a soils testing apparatus as defined in claim 4, the additional characteristic of a plastic enclosure over the top of said apparatus to protect the components thereof.

6. The method of soils percolation rate testing which includes the steps of digging a test hole in a proposed absorption field to a depth of approximately 24 inches (60.96 cm.);

removing any smeared soil to provide a natural soil interface on the walls of the hole;

adding sand or gravel to protect the bottom of the hole from scouring and sediment;

saturating the test hole for at least 4 hours with clear water;

adjusting the water Level in the test hole to a predetermined level corresponding to a selected null point on a calibrated scale; and thereafter measuring any changes in the water level for a finite period of time to yield a direct value of the percolation absorption rate.

7. In combination, a hollow shaft insertable into a test hole;

vertically adjustable wedging blades insertable between the walls of the test hole and said shaft to center the shaft;

pumping means on the shaft to evacuate water from the test hole to a predetermined Level corresponding to a null point on a calibrated scale; and a vertically movable float in said shaft having a float element positioned in the water in the test hole and a rod element extending upwardly adjacent calibrated scale means;

whereby changes in the water level for a finite period of time will yield a direct value of the percolation absorption rate.

8. In combination, a soils testing apparatus comprising an elongated hollow shaft insertable into a test hole and having external T-tracks thereon;

wedging blades slidably insertable in said T-tracks and vertically adjustable to wedgingly lock the shaft in centered alignment in the test hole;

a hand pump on the shaft for evacuating water from the hole to a predetermined null point; and a float and float rod guided and supported within the interior of said shaft including a float for engaging the water in the hole and a movable rod having an end disposed upwardly and outwardly of the shaft; and calibrated scale means adjacent the upper free end of said rod which for a finite period of time will translate movement of the rod into a direct percolation absorption rate.

* * * * *